United States Patent
Krapp et al.

(10) Patent No.: US 9,545,104 B2
(45) Date of Patent: Jan. 17, 2017

(54) LIQUID SUSPENSION CONCENTRATE FORMULATIONS CONTAINING SAFLUFENACIL AND GLYPHOSATE

(75) Inventors: Michael Krapp, Altrip (DE); Wolfgang Gregori, Ludwigshafen (DE); Sven Adam, Steinweiler (DE); Klaus Kolb, Schifferstadt (DE); Jürgen Jakob, Rödersheim-Gronau (DE); Bernd Sievernich, Haßloch (DE); Jörg Steuerwald, Böhl-Iggelheim (DE); Steven Bowe, Apex, NC (US); Joseph Zawierucha, Cary, NC (US); Rex Liebl, Raleigh, NC (US)

(73) Assignee: BASF SE, Ludwigshafen (DE)

( * ) Notice: Subject to any disclaimer, the term of this patent is extended or adjusted under 35 U.S.C. 154(b) by 430 days.

(21) Appl. No.: 13/513,231

(22) PCT Filed: Dec. 8, 2010

(86) PCT No.: PCT/EP2010/069136
§ 371 (c)(1),
(2), (4) Date: Jun. 1, 2012

(87) PCT Pub. No.: WO2011/070054
PCT Pub. Date: Jun. 16, 2011

(65) Prior Publication Data
US 2012/0231954 A1 Sep. 13, 2012

Related U.S. Application Data

(60) Provisional application No. 61/285,020, filed on Dec. 9, 2009.

(51) Int. Cl.
*A01N 57/02* (2006.01)
*A01N 43/54* (2006.01)
*A01N 57/20* (2006.01)

(52) U.S. Cl.
CPC .............. *A01N 43/54* (2013.01); *A01N 57/20* (2013.01)

(58) Field of Classification Search
None
See application file for complete search history.

(56) References Cited

U.S. PATENT DOCUMENTS

| | | | |
|---|---|---|---|
| 4,203,877 A | 5/1980 | Baker | |
| 6,165,940 A * | 12/2000 | Aven | 504/118 |
| 6,479,432 B1 | 11/2002 | Sixl | |
| 7,833,637 B2 | 11/2010 | Tuffe et al. | |
| 8,362,026 B2 | 1/2013 | Schmidt et al. | |
| 2005/0159622 A1 | 7/2005 | Hamprecht et al. | |
| 2006/0293520 A1 | 12/2006 | Hamprecht et al. | |
| 2008/0081211 A1 | 4/2008 | Tuffe et al. | |
| 2008/0293941 A1 | 11/2008 | Gebhardt et al. | |
| 2008/0318781 A1 | 12/2008 | Zagar et al. | |
| 2010/0105562 A1 | 4/2010 | Schmidt et al. | |
| 2012/0149577 A1 | 6/2012 | Krapp et al. | |
| 2012/0157312 A1 | 6/2012 | Krapp et al. | |
| 2012/0231954 A1 | 9/2012 | Krapp et al. | |

FOREIGN PATENT DOCUMENTS

| | | | |
|---|---|---|---|
| EP | 0000424 | 1/1979 | |
| WO | WO 01/22814 | 4/2001 | |
| WO | WO 0130156 | 5/2001 | |
| WO | WO 01/83459 | 11/2001 | |
| WO | WO 03/024221 | * 3/2003 | ............ A01N 43/54 |
| WO | WO 03/097589 | 11/2003 | |
| WO | WO 2005/054208 | 6/2005 | |
| WO | WO 2006/097589 | 9/2006 | |
| WO | WO 2006/125746 | 11/2006 | |
| WO | WO 2007/014758 | 2/2007 | |
| WO | WO 2007/014759 | 2/2007 | |
| WO | WO 2008/043835 | 4/2008 | |
| WO | WO 2011023758 | 3/2011 | |
| WO | WO 2011023759 | 3/2011 | |
| WO | WO 2011070051 | 6/2011 | |

OTHER PUBLICATIONS

Anonymous, "Kixor Herbicide Technical Brochure", BASF Agricultural Products, NC 27709, Jan. 2009, pp. 1-15 (XP000002651574).
International Preliminary Report on Patentability from corresponding International Application No. PCT/EP2010/069136, filed Dec. 8, 2010.
International Search Report in International Application PCT/EP2010/069136, filed Dec. 8, 2010.
English language translation of the International Preliminary Report on Patentability from corresponding International Application No. PCT/EP2010/062471, filed Aug. 26, 2010.
International Search Report in International Application No. PCT/EP2010/062471, filed Aug. 26, 2010.
English language translation of the International Preliminary Report on Patentability from corresponding International Application No. PCT/EP2010/062473, filed Aug. 26, 2012.
International Search Report in International Application No. PCT/EP2010/062473, filed Aug. 26, 2012.

* cited by examiner

Primary Examiner — Alton Pryor
(74) Attorney, Agent, or Firm — Brinks Gilson & Lione

(57) ABSTRACT

The present invention relates to liquid suspension concentrate formulations for plant protection comprising: 2-chloro-5-[3,6-dihydro-3-methyl-2,6-dioxo-4-(trifluoromethyl)-1-(2H)pyrimidinyl]-4-fluoro-N-[[methyl(1-methylethy)amino]sulfonyl]benzamide in the form of the anhydrate; N-(phosphonomethyl)glycine in the form of its free acid, in the form of the ammonium salt or a substituted ammonium salt or a mixture thereof; at least one diluent selected from: hydrocarbon solvents having a boiling point of at least 100° C.; and —$C_1$-$C_8$-alkyl esters of $C_8$-$C_{26}$-fatty acids, mono- and di-$C_1$-$C_4$-alkyl amides of $C_8$-$C_{26}$-fatty acids; optionally at least one diluent that differs from diluents c) and that is selected from organic solvents having at least one oxygen atom; at least one non-ionic surfactant comprising a polyalkoxylate moiety; and at least one anionic surfactant containing a sulfonate group or a sulfate group.

19 Claims, No Drawings

LIQUID SUSPENSION CONCENTRATE FORMULATIONS CONTAINING SAFLUFENACIL AND GLYPHOSATE

This application is a National Stage application of International Application No. PCT/EP2010/069136 filed Dec. 8, 2010, which claims the benefit of U.S. Provisional Application No. 61/285,020, filed Dec. 9, 2009, the entire contents of which are hereby incorporated herein by reference.

The present invention relates to new liquid suspension concentrate formulations containing the herbicides saflufenacil and glyphosate. The invention also relates to the use of the formulations for controlling undesired vegetation and to corresponding methods.

For the purpose of application by the end user, herbicide compounds may be formulated in solid forms, such as wettable powders and granules, as well as in liquid forms, such as emulsifiable concentrates (ECs), aqueous suspension concentrates (SCs) or oil based suspension concentrates (ODs). The latter ones can be diluted with water for use in the field and thus usually provide an easy-to-handle way of application. However, like many active ingredients that are used as herbicides, saflufenacil is only sparingly soluble in water and mixtures of water with water-miscible solvents such as $C_1$-$C_4$-alkanols or $C_2$-$C_4$-alkandiols and -triols. Nonetheless, application of herbicides in the form of dilute aqueous suspension concentrates, i.e. in the form of spray liquors, is favorable for ease of application.

Oil suspension concentrate (OD) formulations contain an active ingredient (a.i.) in the form of finely divided solid particles, which are suspended (dispersed) in a water-immiscible dispersing fluid such as hydrocarbon solvents or fatty acid esters, wherein the active ingredient is usually insoluble or only sparingly soluble (less than 2000 ppm). The dispersing fluid may however include further active ingredients in dissolved form. Suspension concentrates usually utilize surface-active compounds (surfactants), such as dispersants and emulsifying agents for stabilizing the active ingredient particles in the dispersing fluid and for assisting emulsification in water when diluting the OD with water prior to application.

Despite the wide-spread application of ODs, there are a number of problems known to the skilled person which are sometimes encountered with ODs as a result of settling during prolonged storage or storage at elevated temperatures, the resistance of settled particles to re-suspension, the formation of crystalline material upon storage and the separation of an oily phase upon dilution with water. As a consequence, the formulations may be difficult to handle and the bioefficacy may be inconsistent.

Saflufenacil is the common name of 2-chloro-5-[3,6-dihydro-3-methyl-2,6-dioxo-4-(trifluoromethyl)-1-(2H)pyrimidinyl]-4-fluoro-N-[[methyl(1- methylethyl)-amino]sulfonyl]benzamide having the following formula I:

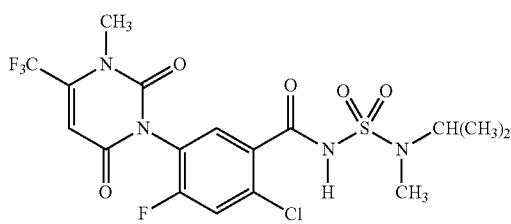

Saflufenacil is an herbicidal active substance which has been disclosed in WO 01/083459. Further processes for its preparation are described in WO 03/097589, WO 05/054208, WO 06/097589 and WO 06/125746. A crystalline and essentially solvent-free form of saflufenacil, herein after also referred to as the crystalline anhydrate form, is disclosed in WO 08/043835.

Glyphosate is the common name of N-(phosphonomethyl)glycine in the form of its free acid having the following formula II:

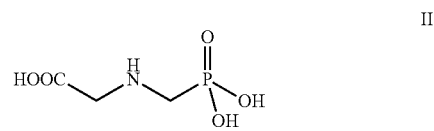

Glyphosate and its salts are non-selective systemic herbicides having a good post-emergence activity against numerous grass weeds. For further reference see for example The Compendium of Pesticide Common Names (http://www.alanwood.net/pesticides/).

When trying to prepare aqueous concentrate formulations of saflufenacil one faces several problems. Due to its N-(aminosulfonyl)-carboxamide side-chain saflufenacil is susceptible to hydrolysis at basic pH values and elevated temperatures. In aqueous media the modifications of saflufenacil, namely crystalline hydrates, a crystalline anhydrate and amorphous forms, may undergo uncontrolled interconversion, which in turn may lead to coarsening of the saflufenacil particles, in particular in aqueous suspension concentrate formulations. These factors might result in a reduced chemical and physical stability of the formulations, especially when stored over prolonged periods of time and/or at elevated temperatures. Said factors may also lead to poor dilution properties as the coarse saflufenacil particles are prone to separate from the diluted formulation. The situation is further complicated when saflufenacil is formulated together with glyphosate, which is typically present in aqueous formulation in dissolved form. Thus, high concentrations of glyphosate may lead to undesired thickening (gelling) of the formulation and may also lead to a demixing of the aqueous phase into water and the surfactants which results in a decreased physical stability of the formulation.

Some of these problems associated with aqueous formulations can possibly be avoided by formulating saflufenacil and glyphosate together as an oil based suspension concentrate (OD). However, OD formulations containing high concentrations of the active ingredients pose the difficulty of dispersing large amounts of saflufenacil and glyphosate particles in the dispersing fluid. Thus, stability problems, in particular upon storage over prolonged periods and/or at elevated temperatures, often have to be overcome.

WO 03/024221 discloses combined applications of herbicidal 3-phenyluracil derivatives with a multitude of other herbicides, including glyphosate. Also disclosed are different formulation types including oily dispersions. However, WO 03/024221 does not describe liquid suspension concentrate formulations containing both saflufenacil and a further herbicide, and in particular does not describe liquid suspension formulations containing both saflufenacil and glyphosate that are stable over extended storage periods.

Up to now, saflufenacil is available in the form of wettable granule formulations and as emulsion concentrate formulations with low a.i. loading. A liquid suspension concentrate formulation of saflufenacil, alone or in combination with a second herbicide, having prolonged storage stability even at elevated temperatures and with good dilution properties has not yet been reported.

Therefore, it is an object of the present invention to provide liquid suspension concentrate formulations that contain saflufenacil and glyphosate. Said formulations should exhibit high physical and chemical stability over prolonged storage periods while maintaining its biological efficacy. Upon dilution with water the formulations should give stable aqueous dilutions containing saflufenacil and glyphosate that do not show formation of sediments and have a high herbicidal activity.

Surprisingly this object could be achieved by formulating the crystalline anhydrate of saflufenacil and glyphosate in the form of its free acid or an ammonium or substituted ammonium salt thereof together with a diluent selected from esters and amides of fatty acids and hydrocarbon solvents, a non-ionic surfactant having a polyalkoxylate moiety and an anionic surfactant having a sulfonate or a sulfate group. In the formulation glyphosate and saflufenacil are present in the form of suspended particles.

Therefore, the present invention relates to a liquid suspension concentrate formulation for plant protection, comprising the components:

a) 2-chloro-5-[3,6-dihydro-3-methyl-2,6-dioxo-4-(trifluoromethyl)-1-(2H)pyrimidinyl]-4-fluoro-N-[[methyl (1-methylethyl)amino]sulfonyl]benzamide in the form of the anhydrate;

b) N-(phosphonomethyl)glycine in the form of its free acid, in the form of the ammonium salt or a substituted ammonium salt or a mixture thereof;

c) at least one diluent selected from:
  c1) hydrocarbon solvents having a boiling point of at least 100° C.; and
  c2) $C_1$-$C_8$-alkyl esters of $C_8$-$C_{26}$-fatty acids, mono- and di-$C_1$-$C_4$-alkyl amides of $C_8$-$C_{26}$-fatty acids;

d) optionally at least one diluent that differs from diluents c) and that is selected from organic solvents having at least one oxygen atom;

e) at least one non-ionic surfactant comprising a polyalkoxylate moiety; and f) at least one anionic surfactant containing a sulfonate group or a sulfate group.

The present invention entails a series of advantages. Particularly, the formulations according to the invention, although containing large amounts of the active ingredients in suspended form, exhibit good physical and chemical stability over prolonged storage times. Thus, neither significant agglomeration of the active ingredients occurs nor does the anhydrate form of saflufenacil degrade to a noticeable extent or change into a different modification even when stored at elevated temperatures for extended time periods. Moreover, the formulations of the invention show outstanding herbicidal activity against a broad spectrum of weeds that have high economical impact.

As used herein, substituted ammonium refers to an ammonium counter ion of a salt, wherein 1, 2, 3, or 4 hydrogen atoms of the ammonium ion are replaced with $C_1$-$C_6$-alkyl radicals which are unsubstituted or substituted with halogen, CN, OH, optionally substituted $C_1$-$C_6$-alkoxy and/or optionally substituted aryl. Examples for substituted ammonium are methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy)-eth-1-ylammonium, di-(2-hydroxyeth-1-yl) ammonium, benzyltrimethylammonium, benzyltriethylammonium.

As used herein, $C_8$-$C_{26}$-fatty acid refers to a fatty acid having from 8 to 26 carbon atoms. Examples for $C_8$-$C_{26}$-fatty acids are the saturated fatty acids caprylic acid, caprinic acid, lauric acid, myristic acid, palmitic acid, margaric acid, stearic acid, arachidic acid, behenic acid, lignoceric acid and cerotic acid; the mono-unsaturated fatty acids undecylenic acid, palmitoleic acid, oleic acid, elaidic acid, vaccenic acid, eicosenic acid, cetoleic acid, erucic acid and nervonic acid; and the poly-unsaturated fatty acids linoleic acid, α-linolenic acid, γ-linolenic acid, arachidonic acid, timnodonic acid, clupanodonic acid and cervonic acid.

As used herein, mono- and di-$C_1$-$C_4$-alkyl amide of a $C_8$-$C_{26}$-fatty acid refer to an amide of a $C_8$-$C_{26}$-fatty acid, as defined herein, that is N-substituted with one and two, respectively, alkyl group(s) having from 1 to 4 carbon atoms. Examples for mono-$C_1$-$C_4$-alkyl amides of $C_8$-$C_{26}$-fatty acids are the mono-methyl amides, mono-ethyl amides, mono-propyl amides, mono-isopropyl amides, mono-butyl amides and mono-isobutyl amides of the aforementioned fatty acids. Examples for di-$C_1$-$C_4$-alkyl amides of $C_8$-$C_{26}$-fatty acids are the di-methyl amides, di-ethyl amides, di-propyl amides, di-isopropyl amides, di-butyl amides, di-isobutyl amides, methyl-ethyl amides, methyl-propyl amides, methyl-isobutyl amides, methyl-tert-butyl amides, ethyl-propyl amides, ethyl-isopropyl amides, ethyl-butyl amides, ethyl-isobutyl amides, propyl-isopropyl amides, propyl-butyl amides and propyl-isobutyl amides of the aforementioned fatty acids.

As used herein, $C_1$-$C_8$-alkyl ester of a $C_8$-$C_{26}$-fatty acid refers to a $C_8$-$C_{26}$-fatty acid, as defined herein, that is esterified with an alkanol having from 1 to 8 carbon atoms. Examples for $C_1$-$C_8$-alkyl esters of $C_8$-$C_{26}$-fatty acids are the methyl esters, ethyl esters, propyl esters, isopropyl esters, butyl esters, isobutyl esters, tert-butyl esters, 1-methyl-propyl esters, pentyl esters, 1-methyl-butyl esters, 2-methyl-butyl esters, 3-methyl-butyl esters, hexyl esters, 1-methyl-pentyl esters, 2-methyl-pentyl esters, 1-ethyl-butyl esters, 1,2,-dimethyl-butyl esters, heptyl esters, 1-methyl-hexyl esters, 2-methyl-hexyl esters, 3-methyl-hexyl esters, 4-methyl-hexyl esters, 5-methyl-hexyl esters, 1-ethyl-pentyl esters, 2-ethyl-pentyl esters, 3-ethyl-pentyl esters, 4-ethyl-pentyl esters, 1,2-dimethyl-pentyl esters, 1,3-dimethyl-pentyl esters, 1,4-dimethyl-pentyl esters, 2,3-dimethyl-pentyl esters and 1-ethyl-2-methyl-butyl esters of the aforementioned fatty acids.

As used herein, $C_4$-$C_{15}$-dialkyl dicarboxylic acid ester refers to a diester of an alkyl dicarboxylic acid with two different or identical alkanols, wherein said diester has from 4 to 15 carbon atoms. Examples for $C_4$-$C_{15}$-dialkyl dicarboxylic acid esters are dimethyl oxalate, ethyl methyl oxalate, diethyl oxalate, ethyl propyl oxalate, ethyl isopropyl oxalate, dipropyl oxalate, propyl isopropyl oxalate, ethyl butyl oxalate, methyl pentyl oxalate, propyl butyl oxalate, dibutyl oxalate, butyl pentyl oxalate, dipentyl oxalate, butyl hexyl oxalate, dimethyl malonate, methyl ethyl malonate, diethyl malonate, propyl ethyl malonate, isopropyl ethyl malonate, methyl propyl malonate, methyl isopropyl malonate, dipropyl malonate, ethyl pentyl malonate, dibutyl malonate, dipentyl malonate, pentyl hexyl malonate, dihexyl malonate, dimethyl succinate, ethyl methyl succinate, diethyl succinate, methyl propyl succinate, methyl isopropyl succinate, ethyl propyl succinate, dipropyl succinat, diisopropyl succinate, diisobutyl succinate, dipentyl succinate, dimethyl glutarate, ethyl methyl glutarate, diethyl glutarate, diisopropyl glutarate, diisobutyl glutarate, ethyl pentyl glutarate, dicyclopentyl glutarate, dimethyl adipate, ethyl methyl adipate, dipropyl adipate, diisobutyl adipate, ethyl propyl adipate, dimethyl pimelate, diethylpimelate, dipropyl pimelate, propyl butyl pimelate and diisobutyl pimelate.

As used herein, N-$C_5$-$C_{15}$-alkyl pyrrolidone refers to a N-alkylated derivative of pyrrolidone having from 5 to 15 carbon atoms. Examples of N-$C_5$-$C_{15}$-alkyl pyrrolidone are N-methyl pyrrolidone, N-ethyl pyrrolidone, N-propyl pyrrolidone, N-isopropyl pyrrolidone, N-butyl pyrrolidone, N-isobutyl pyrrolidone, N-pentyl pyrrolidone, N-hexyl pyrrolidone, N-(4-ethyl-pentyl) pyrrolidone, N-octyl pyrrolidone, N-nonyl pyrrolidone, N-decyl pyrrolidone and N-(7-methyl-decyl) pyrrolidone.

As used herein, $C_2$-$C_6$-lactone refers to an internal cyclic ester of a hydroxylated alkanoic acid having from 2 to 6 carbon atoms. An example for a $C_2$-$C_6$-lactone is γ-butyrolactone.

As used herein, $C_3$-$C_4$-alkylene oxide refers to an epoxide ring wherein the carbon atoms of the epoxide ring is substituted with one or two methyl groups or with one ethyl group. Specifically, $C_3$-$C_4$-alkylene oxide refers to propylene oxide, 1,2-butylene oxide, cis- or trans-2,3-butylene oxide and/or isobutylene oxide.

As used herein "concentrate formulation" refers to a pesticidal formulation that contains at least 10% by weight, preferably at least 15% by weight and in particular at least 25% by weight, based on the total weight of the formulation, of active ingredients.

As stated before, the crystalline anhydrate form of saflufenacil employed in the formulation of the invention refers to the saflufenacil modification that is disclosed in WO 08/043835. Accordingly, the crystalline anhydrate form is an essentially solvent-free crystalline form of saflufenacil (compound of formula I), herein also referred to as saflufenacil anhydrate. In this connection the term "essentially solvent-free" means that the crystalline anhydrate form comprises no detectable amounts of solvents incorporated into the crystal lattice, i.e. the amount of solvent in the crystal lattice is less than 10 mol %, in particular not more than 5 mol %, based on saflufenacil.

The crystalline anhydrate form can be identified by means of X-ray powder diffractometry on the basis of its diffraction diagram. Thus, an X-ray powder diffractogram recorded at 25° C. using Cu-Ka radiation (1.54178 Å) shows at least 2, as a rule at least 4, frequently at least 6, in particular at least 8 and specifically all of the reflexes detailed in Table 1 hereinbelow as 2θvalues, or as interplanar spacings d:

TABLE 1

| 2θ | d [Å] |
|---|---|
| 6.3 ± 0.2° | 14.92 ± 0.3 |
| 9.4 ± 0.2° | 9.37 ± 0.2 |
| 10.9 ± 0.2° | 8.15 ± 0.1 |
| 11.9 ± 0.2° | 7.45 ± 0.05 |
| 12.6 ± 0.2° | 7.02 ± 0.05 |
| 15.0 ± 0.2° | 5.90 ± 0.05 |
| 15.8 ± 0.2° | 5.62 ± 0.04 |
| 17.1 ± 0.2° | 5.19 ± 0.03 |
| 20.0 ± 0.2° | 4.44 ± 0.02 |
| 20.4 ± 0.2° | 4.36 ± 0.02 |
| 24.7 ± 0.2° | 3.61 ± 0.02 |
| 25.2 ± 0.2° | 3.53 ± 0.02 |
| 26.2 ± 0.2° | 3.40 ± 0.02 |

Studies on monocrystals of the anhydrate form at −170° C. demonstrate that the underlying crystal structure is monoclinic. The unit cell has the space group P2(1)/c. The characteristic data of the crystal structure of the anhydrate form are compiled in Table 2.

TABLE 2

Crystallographic characteristics of the crystalline anhydrate form (measured at −170° C.)

| Parameter | Form II |
|---|---|
| class | monoclinic |
| space group | P2(1)/c |
| a | 9.377(5) Å |
| b | 7.698(4) Å |
| c | 28.12(2) Å |
| α | 90° |
| β | 96.37(3)° |
| γ | 90° |
| volume | 2017.1(17) Å 3 |
| Z | 4 |
| density (calculated) | 1.649 mg/m$^3$ |
| R1; wR2 | 0.057; 0.149 |
| wavelength | 1.54178 Å | a, b, c = unit cell length
α, β, γ = unit cell angle
Z = number of molecules in the unit cell Besides X-ray powder diffractometry and the crystallographic analysis, differential scanning calorimetry (DSC) can also be employed for identifying the anhydrate form. Thus, the anhydrate form shows a thermogram with a characteristic melting peak in the range between 170 and 200° C. The peak maximum is typically in the range of approximately 180° C. to 190° C. The melting points indicated herein refer to data determined by means of DSC, crucible material aluminum, heating rate 5 K/min).

The crystalline saflufenacil anhydrate may be prepared by controlled crystallization from a solution of saflufenacil in an organic solvent which is essentially free from water as described in WO 08/043835.

In the formulations according to the invention the saflufenacil anhydrate is present predominantly in the form of finely divided solid particles which are suspended in the organic diluent. Likewise, glyphosate, particularly if present in the form of its free acid or its ammonium salt, in general is also included in the formulation as finely divided solid particles suspended in the organic diluent. The formulations according to the invention are therefore also referred to as oil suspension concentrates. The oil suspension concentrates of the invention can also comprise a small amount of saflufenacil anhydrate and/or a small amount of glyphosate in dissolved form. The amount of dissolved active saflufenacil anhydrate will, as a rule, not exceed 20% by weight, in particular 10% by weight, based on the total amount of the saflufenacil anhydrate which is present in the formulation. The amount of dissolved glyphosate will, particularly if present in the form of its free acid or its ammonium salt, as a rule, not exceed 10% by weight, in particular 5% by weight, based on the total amount of the glyphosate which is present in the formulation. The particle size of the suspended particles is in the range which is typical of oil suspension concentrates. As a rule, the particles have a mean particle diameter, herein also termed D50 value, in the range from 0.5 to 20 µm, in particular in the range from 0.8 to 10 µm. The Dm-value is defined as the value that is above the diameters of 50% by weight of the particles and below the diameters of 50% by weight of the particles. Preferably, at least 80% by weight, in particular at least 90% by weight, of the particles have particle sizes in the stated ranges. A particle size that is not exceeded by the diameters of at least 90% by weight of the particles is herein also termed the Dm-value. In general, the Dm-value of the suspended a.i. particles of the formulation according to the invention will not exceed 20 pm, preferably not exceed 10 µm and in particular not exceed 5 µm. Advantageously, at least 40% by weight, preferably at least 60% by weight and in particular at least 80% by weight of the particles have a particle diameter of below 8 µm or even below 5 µm. The particle size of the active substance particles can be determined by conventional methods such as light-scattering.

The particles of saflufenacil anhydrate (component a)) contained in the formulation of the invention are solid a.i. particles, i.e. the particles mainly contain pure component a). The purity of the component a) is usually at least 90% by weight, preferably at least 95% and in particular at least 97% by weight. Likewise, the particles of glyphosate (component b)) contained in the formulation of the invention are solid a.i. particles, i.e. the particles mainly contain pure component b). The purity of the component b) is usually at least 90% by weight, preferably at least 95% and in particular at least 97% by weight.

The concentration of component a) in the formulation of the invention is typically in the range of from 0.1 to 20% by weight, in particular in the range of from 0.5 to 13% by weight, and specifically in the range of from 1 to 8% by weight, based on the total weight of the formulation.

The concentration of component b) in the formulation of the invention, with component b) being calculated as glyphosate acid form, is typically in the range of from 10 to 55% by weight, in particular in the range of from 20 to 45% by weight, and specifically in the range of from 28 to 37% by weight, based on the total weight of the formulation.

In the liquid suspension concentrate formulations of the invention the weight ratio of component a) to component b), with component b) being calculated as glyphosate acid form, is usually in the range of from 1:1 to 1:50, preferably in the range of from 1:2 to 1:20, in particular in the range of from 1:3 to 1:16 and specifically in the range from 1:5 to 1:14. Particularly preferred are the weight ratios of components a) to b) of about 1:6.5 and of about 1:13.

The total amount of the active substances components a) and b) will, as a rule, not exceed 60% by weight, in particular 50% by weight, based on the total weight of the formulation according to the invention and is typically in the range from 10 to 60% by weight, in particular in the range from 20 to 50% by weight and specifically in the range of from 29 to 45% by weight, based on the total weight of the formulation according to the invention.

The at least one diluent c) contained in the formulations according to the invention is selected among, as diluents c1), hydrocarbon solvents having a boiling point of at least 100° C., and, as diluents c2), $C_1$-$C_8$-alkyl esters of $C_8$-$C_{26}$-fatty acids and mono- and di-$C_1$-$C_4$-alkyl amides of $C_8$-$C_{26}$-fatty acids, and mixtures thereof. Among these, those solvents and solvent mixtures are preferred which are liquid under standard conditions.

In this context "liquid" means that the diluent has, under standard conditions, a dynamic viscosity at 20° C. of, as a rule, no more than 150 mPa·s, in particular no more than 100 mPa·s, specifically no more than 50 mPa·s, in particular in the range of from 1 to 150 mPa·s, preferably in the range of from 2 to 100 mPa·s and in particular in the range of from 3 to 50 mPa·s (determined as specified in AS™ D 445).

Diluents c1) of the formulations according to the present invention are preferably chosen from aliphatic hydrocarbon solvents and aromatic hydrocarbon solvents, which all have boiling points of at least 100° C. and preferably boiling points in the range of from 170 to 310° C. (as general reference for hydrocarbons see, for example, Rompp Lexikon Chemie, 10th edition, volume 3, page 2202 (1997), Georg Thieme Verlag Stuttgart/New York).

In this context aliphatic hydrocarbon solvents with a boiling point of at least 100° C. particularly refer to saturated and unsaturated hydrocarbons that may optionally include a non-aromatic carbocycle, such as linear, branched and cyclic alkanes and alkenes, that have boiling points in the stated range and include 7 to about 18 carbon atoms, and in particular also to mixtures of these aliphatic hydrocarbons. Such mixtures are commercially available e.g. under the trade name Exxsol which denotes products that predominantly contain kerosene having been depleted of aromatic components, such as Exxsol™ D30, Exxsol™ D40, Exxsol™ D80, Exxsol™ D100, Exxsol™ D120 and Exxsol™ D220/230. An example of an aliphatic hydrocarbon having a carbocycle is limonene.

In the context of the invention aromatic hydrocarbon solvents with a boiling point of at least 100° C. particularly refer to mono- or polycyclic aromatic compounds which optionally may carry one or more aliphatic or araliphatic substituents, in particular alkyl and arylalkyl moieties, and which have boiling points in the stated range. Said aromatic hydrocarbon solvents preferably refer to mixtures of such aromatic compounds that are obtained by distillation in particular from crude oil products as fractions in the given boiling point range, such as the commercial products known under the trade names Solvesso®, in particular Solvesso® 100, Solvesso® 150, Solvesso® 200, Solvesso® 150 ND and Solvesso® 200 ND, Aromatic®, in particular Aromatic® 150 and Aromatic® 200, Hydrosol®, in particular Hydrosol® A 200 and Hydrosol® A 230/270, Caromax®, in particular Caromax® 20 and Caromax® 28, Aromat K 150, Aromat K 200, Shellsol , in particular Shellsol® A 100 and Shel!sof' A 150, and Fin FAS-TX, in particular Fin FAS-TX 150 and Fin FAS-TX 200. Particularly preferred are the mixtures Solvesso® 150 ND and Solvesso® 200 ND (ExxonMobil Chemical), which are depleted of the potential carcinogen naphthalene. Thus, Solvesso® 150 ND mainly contains aromatic hydrocarbons having 10 or 11 carbon atoms which boil in the range of from 175 to 209° C. and primarily consist of alkylbenzenes, whereas Solvesso® 200 ND mainly contains aromatic hydrocarbons having 10 to 14 carbon atoms which boil in the range of from 235 to 305° C. and primarily consist of alkylnaphthalenes. Another example for said aromatic hydrocarbon solvents is a product known under its tradename Hisol SAS-296 that consists of a mixture of 1-phenyl-1-xylylethane and 1-phenyl-1-ethyl-phenylethane.

Particularly preferred diluents c1) are the aforementioned aromatic hydrocarbon solvents, in particular those mentioned herein as preferred.

Preferred diluents c2) are the $C_1$-$C_4$-alkyl esters of $C_{12}$-$C_{22}$-fatty acids, in particular the methyl esters of saturated or mono-unsaturated $C_{14}$-$C_{18}$-fatty acids, and mono- or di-$C_1$-$C_3$-alkyl amides of $C_{12}$-$C_{22}$-fatty acids, in particular the mono-methyl amides, mono-ethyl amides, di-methyl amides and di-ethyl amides of saturated or mono-unsaturated $C_{14-18}$-fatty acids.

According to a preferred embodiment of the invention the at least one diluent c) is selected from diluents c1) or from diluents c2), in particular from those mentioned herein as preferred.

According to a particular preferred embodiment of the invention the component c) comprises at least one diluent c1) and at least one diluent c2), in particular those mentioned herein as preferred.

The total amount of diluents c) will, as a rule, not exceed 80% by weight, in particular 65% by weight, based on the total weight of the formulation according to the invention and is typically in the range from 15 to 80% by weight, in particular in the range from 25 to 65% by weight and specifically in the range of from 30 to 55% by weight, based on the total weight of the formulation according to the invention.

The formulations of the present invention may optionally further contain at least one liquid diluent d) that differs from diluents c) and is an organic solvent having at least one oxygen atom. Diluents d) may be selected from $C_1$-$C_{10}$-alcohols, including alcohols having at least one ether group or at least one keto group, $C_3$-$C_{14}$-esters other than those of component c), including diesters and $C_2$-$C_6$-lactones, amides other than those of component c), ethers, ketons, aldehydes, N-alkyl-$C_3$-$C_5$-lactams, N,N'-dimethyl-$C_3$-$C_5$-alkylene ureas, $C_2$-$C_4$-alkylene carbonates, tri-$C_1$-$C_4$-alkyl phosphates, DMSO and the like. Preferred diluents d) are selected from $C_4$-$C_{15}$-dialkyl dicarboxylic acid esters, in particular dimethyl and diethyl $C_3$-$C_{10}$-dicarboxylic acid esters, N-$C_5$-$C_{15}$-alkyl pyrrolidones, in particular N-$C_5$-$C_8$-alkyl pyrrolidones, $C_3$-$C_5$-lactones, in particular γ-butyrolactone, and DMSO.

The total amount of diluents d), if present, is preferably in the range from 0.5 to 35% by weight, in particular from 1 to 30% by weight, more preferably from 5 to 25% by weight, based on the total weight of the formulation.

According to another preferred embodiment of the invention the component c) comprises at least one diluent c1) and the component d) comprises at least one diluent that is preferably selected from dimethyl and diethyl $C_3$-$C_{10}$-dicarboxylic acid esters.

The formulations of the invention also include, as component e), at least one non-ionic surfactant that comprises a polyalkoxylate moiety, such as in particular an ethylene oxide polymer moiety or an ethylene oxide/$C_3$-$C_4$-alkylene oxide block copolymer moiety. Surfactants e) are preferably selected from the surfactant groups e1), e2), e3) and e4) as defined herein below.

The non-ionic surfactants of group e1) are selected from polyethoxylates and poly-ethoxylates-co-propoxylates of linear or branched $C_3$-$C_{22}$-alkanols, such as polyethoxylated or poly-ethoxy-co-propoxylated $C_8$-$C_{22}$-fatty alcohols and poly-ethoxy-co-propoxylated $C_3$-$C_{20}$-oxoalcohols. Examples of non-ionic surfactants e1) are polyethoxylated decanol, polyethoxylated lauryl alcohol, polyethoxylated isotridecanol, polyethoxylated cetyl alcohol, poly-ethoxylates-co-propoxylates of octanol, poly-ethoxylates-co-propoxylates of 2-ethyl-hexanol, poly-ethoxylates-co-propoxylates of nonanol, poly-ethoxylates-co-propoxylates of 3-propyl-heptanol, poly-ethoxylates-co-propoxylates of 2-ethyl-octanol, poly-ethoxylates-co-propoxylates of butanol, poly-ethoxylates-co-propoxylates of iso-butanol, and poly-ethoxylates-co-propoxylates of decanol. Preferred non-ionic surfactants e1) are polyethoxylates of $C_8$-$C_{16}$-alkanols and particularly preferred are polyethoxylates of $C_{10}$-$C_{13}$-alkanols. The non-ionic surfactants of the group e1) described herein are commercially available e.g. under the trade names Lutensol® ON (BASF), Lutensol® TO (BASF) and Atlas® G 5000 (Uniqema).

The non-ionic surfactants of group e2) are selected from fatty acid polyalkoxylates and triglyceride polyalkoxylates, such as the Serdox® NOG products (Condea), from polyalkoxylated animal fats, such as lard, tallow, milkfat, cod liver oil and whale oil, and from polyalkoxylated vegetable oils, such as soya oil, rapeseed oil, corn oil, sunflower oil, cotton seed oil, linseed oil, coconut oil, palm oil, safflower oil, walnut oil, peanut oil, olive oil or castor oil. Preferred non-ionic surfactants e2) are polyalkoxylated and in particular polyethoxylated vegetable oils, in particular rapeseed oil and castor oil. Products comprising polyethoxylated castor oil are commercially available e.g. under the trade names Wettol® EM (BASF), Emulsogen® EL (Clariant) and Emulan® EL (BASF).

The non-ionic surfactants of group e3) are selected from non-ionic block copolymers comprising at least one poly (ethylene oxide) moiety PEO and at least one polyether moiety PAO derived from $C_3$-$C_4$-alkylene oxides. The at least one PAO moiety of a non-ionic block copolymer e3) usually comprises at least 3, preferably at least 5, in particular 10 to 100 repeating units (number average) which are derived from $C_3$-$C_4$ alkylene oxides, such as propylene oxide, 1,2-butylene oxide, cis- or trans-2,3-butylene oxide or isobutylene oxide. Preferably, the PAO moieties comprise at least 50% by weight, and more preferably at least 80% by weight of repeating units derived from propylene oxide. The at least one PEO moiety of a non-ionic block copolymer e3) usually comprise at least 3, preferably at least 5, and more preferably at least 10 repeating units derived from ethylene oxide (number average). The weight ratio of PEO moieties and PAO moieties (PEO:PAO) usually ranges from 1:10 to 10:1, preferably from 2:8 to 7:3 and in particular from 3:7 to 6:4. Suitable surfactants e3) are described e.g. in WO 06/002984, in particular those having the formulae P1 to P5 given therein. Preferred non-ionic surfactants e3) are selected from ethylene oxide/propylene oxide block copolymers, in particular those that have the aforementioned preferred properties. The non-ionic surfactants e3) are commercially available e.g. under the trade names Pluronic® (BASF), such as Pluronic® PE and Pluronic® RPE.

The non-ionic surfactants of group e4) are selected from polyethoxylates of polyol esters, wherein the polyols may be partially or completely esterified with saturated or unsaturated $C_6$-$C_{22}$-alkanoic acids, such as mono-, di- and triesters of glycerine and mono-, di-, tri-, tetra-, penta- and hexaesters of sorbitol, e.g. glycerine monostearate, sorbitol monooleat and sorbitol hexaoleat. Preferred non-ionic surfactants e4) are polyethoxylates of esters of sorbitol with $C_6$-$C_{22}$-alkanoic acids, in particular preferred are polyethoxylates of sorbitol hexaoleate. The non-ionic surfactants of the group e4) described herein are commercially available e.g. under the trade name Atlas G 1086 (Croda).

The terms polyalkoxylate and polyalkoxylated used herein refer to polyether radicals derived from alkylene oxide, in particular $C_2$-$C_4$-alkylene oxide, such as ethylene oxide and $C_3$-$C_4$-alkylene oxide. Likewise, the terms polyethoxylate and polyethoxylated used herein refer to polyether radicals derived from ethylene oxide. Correspondingly, the terms poly-ethoxy-co-propoxylate and poly-ethoxy-co-propoxylated refer to a polyether radical derived from a mixture of ethylene oxide and propylene oxide. Thus, polyethoxylates have repeating units of the formula [$CH_2CH_2O$] while poly-ethoxy-co-propoxylates have repeating units of the formulae [$CH_2CH_2O$] and [$CH(CH_3)CH_2O$]. In the surfactants of these groups, the number of such repeating units will generally range from 2 to 200, in particular from 3 to 100, especially from 3 to 50.

Particularly preferred non-ionic surfactants e) are selected from the surfactants of groups e1) and e2), specifically from those surfactants of groups e1) and e2) mentioned herein as preferred.

According to preferred embodiment of the invention the component e) comprises at least 2 different non-ionic surfactants, which are preferably selected from polyethoxylates of $C_8$-$C_{22}$-alkanols, poly-ethoxylates-co-propoxylates of $C_3$-$C_{22}$-alkanols, polyethoxylates of vegetable oils and polyethoxylates of animal fats.

According to particularly preferred embodiment of the invention the component e) comprises at least one polyethoxylate of a $C_8$-$C_{22}$-alkanol and at least one polyethoxylate of a vegetable oil.

The total amount of non-ionic surfactants e) will, as a rule, not exceed 35% by weight, in particular 25% by weight, based on the total weight of the formulation according to the invention and is typically in the range from 1 to 35% by weight, in particular in the range from 2 to 25% by weight and specifically in the range of from 3 to 20% by weight, based on the total weight of the formulation according to the invention.

The formulations of the invention also include, as component f), at least one anionic surfactant that contains a sulfonate group or a sulfate group. Surfactants f) are preferably selected from the surfactant groups f1), f2), f3), f4), f5), f6), f7) and f8) as defined herein below.

The anionic surfactants of group f1) are selected from $C_1$-$C_{16}$-alkylarene sulfonates, such as mono-, di- and tri-$C_1$-$C_{16}$-alkylbenzene sulfonates and mono-,di- and tri-$C_1$-$C_{16}$-alkylnaphthaline sulfonates. Examples of anionic surfactants of group f1) are dibutylnaphtaline sulfonate, dodecyldiphenylether sulfonate, cumyl sulfonate, octylbenzene sulfonate, nonylbenzene sulfonate, dodecylbenzene sulfonate and tridecylbenzene sulfonate. Preferred surfactants f1) are mono- or di-$C_4$-$C_8$-alkylnaphthaline sulfonic acids and mono- or di-$C_4$-$C_{16}$-alkylbenzene sulfonic acids and the alkaline metal salts, such as the sodium or potassium salts, and the earth alkaline metal salts, in particular the calcium salts, and the ammonium salts thereof. The anionic surfactants f1) are commercially available e.g. under the trade name Wettol® EM1 (BASF), Wettol® NT1 (BASF), Rhodacal® 70 (Rhodia) and Lutensit® A-LBS (BASF).

The anionic surfactants of group f2) are selected from the alkaline metal salts, the earth alkaline metal salts and the ammonium salts of sulfated polyethoxylates of mono-, di- or tristyryl phenols. Preferred surfactants f2) are the ammonium salts of sulfated polyethoxylates of tristyryl phenols, in particular of 2,4,6-tristyryl phenols. The anionic surfactants f2) are commercially available e.g. under the trade name Soprophor® 4D 384 (Rhodia).

The anionic surfactants of group f3) are selected from the alkaline metal salts, the earth alkaline metal salts and the ammonium salts of di-$C_4$-$C_{16}$-alkylesters of sulfosuccinic acid. Preferred surfactants f3) are the sodium, potassium, calcium or ammonium salts of di-$C_6$-$C_{12}$-alkylesters of sulfosuccinic acid, in particular the sodium salt of dioctylsulfosuccinate. The anionic surfactants f3) are commercially available e.g. under the trade name Aerosol® OT-A (Cytec).

The anionic surfactants of group f4) are selected from polymeric anionic surfactants having $SO_3$-groups bound to an aromatic moiety such as a phenyl or a naphthyl ring, e.g. condensates of arylsulfonic acid with formaldehyde and optionally in addition with urea, such as naphthalene sulfonic acid formaldehyde condensates, phenol sulfonic acid formaldehyde condensates, cresol sulfonic acid formaldehyde condensates, ligninsulfonates, etc. The arylsulfonic acids incorporated into said formaldehyde condensates may be e.g. phenol sulfonic acids or naphthalene sulfonic acids which are unsubstituted or substituted by one or more, e.g. 1, 2, 3 or 4 $C_1$-$C_{20}$ alkyl groups. Preferred surfactants f4) are the alkaline metal salts or earth alkaline metal salts of reaction products (condensates) of phenol sulfonic acid and formaldehyde. The anionic surfactants f4) are commercially available e.g. under the trade names Tamol® DN (BASF), Tamol® PP and Wettol® D1 (BASF).

The anionic surfactants of group f5) are selected from the sodium, potassium, calcium and ammonium salts of $C_6$-$C_{22}$-alkyl sulfonates and $C_6$-$C_{22}$-alkyl sulfates, such as lauryl sulfonate, isotridecyl sulfonate, lauryl sulfate, isotridecyl sulfate, cetyl sulfate and stearyl sulfate.

The anionic surfactants of group f6) are selected from the sodium, potassium, calcium and ammonium salts of sulfates and sulfonates of $C_6$-$C_{22}$-fatty acids and $C_6$-$C_{22}$-fatty acid esters.

The anionic surfactants of group f7) are selected from the sodium, potassium, calcium and ammonium salts of sulfates of polyethoxylated $C_6$-$C_{22}$ alkanols, such as sulfates of polyethoxylated lauryl alcohol.

The anionic surfactants of group f8) are selected from the sodium, potassium, calcium and ammonium salts of sulfates of polyethoxylated $C_4$-$C_{16}$-alkylphenols.

Particularly preferred anionic surfactants f) are selected from the surfactants of groups f1), f2) and f3), specifically from those surfactants of groups f1), f2) and f3) mentioned herein as preferred.

According to preferred embodiment of the invention the component f) comprises at least 2 different anionic surfactants, which are preferably selected from surfactants of groups f1), f2) and f3) that are mentioned herein above as preferred.

The total amount of anionic surfactant f) will, as a rule, not exceed 35% by weight, in particular 25% by weight, based on the total weight of the formulation according to the invention and is typically in the range from 0.5 to 40% by weight, in particular in the range from 1 to 27% by weight and specifically in the range of from 2 to 22% by weight, based on the total weight of the formulation according to the invention.

The aforementioned surfactants, which may also be referred to as surface-active substances, are known to the skilled worker. An overview can be found, for example, in McCutcheon's "Detergents and Emulsifiers Annual", MC Publ. Corp., Ridgewood N.J.; Sisley and Wood, "Encyclopedia of Surface active Agents", Chem. Publ. Co. Inc, N.Y. 1964; Schönfeldt, "Grenzflächenaktive Äthylenoxidaddukte" [Interface-active ethylene oxide adducts], Wiss. Verlagsgesellschaft, Stuttgart 1976; Winnacker-Küchler, "Chemische Technologie" [Chemical technology], volume 7, C. Hauser-Verlag, Munich, 4th edition 1986.

According to yet another preferred embodiment of the present invention the formulation of the invention comprises:

from 0.5 to 13% by weight, preferably from 1 to 8% by weight, based on the total weight of the composition, of saflufenacil in the form of its crystalline anhydrate;

from 20 to 45% by weight, preferably from 28 to 37% by weight, based on the total weight of the composition, of glyphosate in the form of its free acid, in the form of its ammonium salt or its substituted ammonium salt, or a mixture thereof;

from 25 to 65% by weight, preferably from 30 to 55% by weight, based on the total weight of the composition, of at least one diluent c) selected from:

c1) hydrocarbon solvents having a boiling point of at least 100° C.; and c2) $C_1$-$C_8$-alkyl esters of $C_8$-$C_{26}$-fatty acids, mono- and di-$C_1$-$C_4$-alkyl amides of $C_8$-$C_{26}$-fatty acids;

from 0 to 30% by weight, preferably from 0 to 25% by weight, based on the total weight of the composition, at least one diluent that differs from diluents c) and that is selected from organic solvents having at least one oxygen atom;

from 2 to 25% by weight, preferably from 3 to 20% by weight, based on the total weight of the composition, of at least one non-ionic surfactant comprising a polyalkoxylate moiety; and from 1 to 27% by weight, preferably from 2 to 22% by weight, based on the total weight of the composition, of at least one anionic surfactant containing a sulfonate group or a sulfate group.

The compositions according to the invention may also comprise customary adjuvants, such as viscosity-modifying additives (thickeners), anti-drift agents, adhesives, penetrants, antifoam agents, preservatives, inorganic dispersants, antifreeze agents, antioxidants, colorants, aromatic substances, etc, which are usually employed in oil formulations of herbicides. The amount of additives will generally not exceed 15% by weight, in particular 10% by weight of the total weight of the composition.

Suitable thickeners are compounds which affect the rheological properties of the oil suspension concentrate, even when used in small amounts. These include in particular all substances which increase the viscosity of oils, specifically those which are suitable for plant protection formulations.

Examples of suitable thickeners are:

g1) natural silicates and modified natural silicates, such as chemically modified bentonites, hectorites, attapulgites, montmorillonites, smectites or other silicate minerals, such as Bentone® (Elementis), Attagel® (Engelhard), Agsorb® (Oil-Dri Corporation) or Hectorite® (Akzo Nobel), preferably Bentone®, g2) synthetic silicates or silicic acids, in particular highly disperse silicates and silicic acids from the Sipernat®, Aerosil® or Durosil® series (Degussa), the CAB-O-SIL® series (Cabot) or the Van Gel series (RT. Vanderbilt), g3) organic thickeners, for example those based on hydrogenated fatty acids and fatty acid derivatives, such as thickeners from the Thixin® or Thixatrol® series (Elementis), and thickeners based on synthetic polymers, for example polyalkyl(meth)acrylates, polyamide thickeners, polyurethane thickeners, xanthan gum, for example the products sold under the name Rhodopol® (Rhodia) and Kelzan® S (Kelco Corp.).

Preferred thickeners are those based on natural or synthetic silicates and silicic acids, for example the substances mentioned in groups g1) and g2).

Suitable inorganic dispersants, also termed anticaking agents, for preventing agglutination of the a.i. particles, are silica (such as, for example Sipernat® 22 from Degussa), alumina, calcium carbonate and the like. In the context of the present invention silica is a preferred inorganic dispersant. The concentration of inorganic dispersants in the final aqueous concentrates will generally not exceed 5% by weight, based on the total weight of the final aqueous concentrate, and is preferably in the range from 0.01 to 5% by weight, in particular from 0.02 to 3% by weight and especially from 0.1 to 2.5% by weight, based on the total weight of the final suspension concentrate.

Suitable antifreeze agents are those from the group of the ureas, diols and polyols, such as ethylene glycol and propylene glycol. Suitable antifoams are those based on silicones. Suitable preservatives, colorants and perfumes are known to the skilled worker, for example from the literature mentioned above in connection with surfactants, and from Watkins, "Handbook of Insecticide Dust Diluents and Carriers", 2nd Ed., Darland Books, Caldwell N.J.; H. v. Olphen, "Introduction to Clay Colloid Chemistry"; 2nd Ed., J. Wiley & Sons, N.Y.; and C. Marsden, "Solvents Guide"; 2nd Ed., Interscience, N.Y. 1963.

The oil suspension concentrates according to the invention can be prepared by methods known per se for the preparation of oil suspension concentrates, for example by mixing components a) to f) and, if appropriate further adjuvants. Thus, it is possible for example to initially introduce component c) and optionally component d), followed by the addition of components a), b), e), f), if appropriate residual amounts of c) and d), and, if appropriate, further adjuvants. If appropriate, c) optionally together with d), may also be mixed with a thickener before the remaining components are added. The resulting oil suspension can subsequently be subjected to fine-milling, if appropriate after a preliminary milling. Milling and grinding are used synonymously herein to refer to any suitable physical attrition method, such as grinding, crushing or milling.

Customary mixing devices which, if appropriate, can be heated may be used for preparing the mixtures. For the preliminary milling step, it is possible to use, for example, high-pressure homogenizers or mills which operate on the rotor-stator principle, such as Ultraturax homogenizers, for example from IKA, or toothed colloid mills, for example from Puck. Apparatus which can be used for the fine-grinding step can be, for example, batchwise-operating bead mills, for example from Drais, or continuously-operating bead mills, for example from Bachofen. Depending on the properties of the components employed, and on process-engineering and safety aspects and economical reasons, the preparation process can be adapted and, if appropriate, a pre-grinding step or else a fine-grinding step can be dispensed with.

By means of the aforementioned one or more milling steps the particle sizes of the particles of components a) and b) present in the suspension are typically reduced to below 20 µm, preferably to below 10 µm and in particular to below 5 µm ($D_{90}$-value).

Components a) to f) and, if appropriate, further adjuvants, which are employed for the preparation of the formulations may comprise, as secondary component, water, which is recovered in the oil suspension concentrates according to the invention. Therefore, the oil suspension concentrates according to the invention may comprise small amounts of water, in general no more than 5% by weight, in particular no more than 1% by weight, based on the total weight of the formulation.

The invention also relates to uses of the liquid suspension concentrate formulation of the invention for protecting crop plants and to methods of controlling undesired vegetation, which comprise applying the formulations, in diluted or undiluted form, to plants, their environment and/or seeds.

The herbicidal formulations of the invention affect a very good control of vegetation in non-crop areas, especially at high application rates. In crops such as soybean, cotton, oilseed rape, flax, lentils, rice, sugar beet, sunflower, tobacco and cereals, such as, for example maize or wheat, they are active against broad-leaved weeds and grass weeds without inflicting substantial damage to the crop plants. This effect is particularly observed at low application rates.

Depending on the application method in question, the formulations of the invention can additionally be employed in a further number of crop plants to remove undesired plants. Crops which are suitable are, for example, the following:

*Allium cepa, Ananas comosus, Arachis hypogaea, Asparagus officinalis, Beta vulgaris* spec. *altissima, Beta*

*vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum* (*N.rustica*), *Olea europaea, Oryza sativa, Phaseolus lunatus, Phaseolus vulgaris, Picea abies, Pinus* spec., *Pisum sativum, Prunus armeniaca, Prunus avium, Prunus cerasus, Prunus dulcis, Prunus domesticua, Prunus persica, Pyrus communis, Ribes sylvestre, Ricinus communis, Saccharum officinarum, Secale cereale, Solanum tuberosum, Sorghum bicolor* (s. *vulgare*), *Theobroma cacao, Trifolium pratense, Triticum aestivum, Triticum durum, Vicia faba, Vitis vinifera* and *Zea mays.*

In addition, the formulations of the invention can also be used in crops which tolerate the effect of herbicides as the result of breeding, including genetic engineering methods.

Furthermore, the formulations of the invention can also be used in crops which tolerate attack by insects or fungi as the result of breeding, including genetic engineering methods.

Moreover, it has been found that the formulations of the invention are also suitable for the defoliation and desiccation of plant parts, for which crops plants such as cotton, potato, oilseed rape, sunflower, soybean or field beans, in particular cotton, are suitable.

As desiccants, the formulations of the invention are particularly suitable for desiccating the aerial parts of crop plants such as potato, oilseed rape, sunflower and soybean. This makes possible the fully mechanical harvesting of these important crop plants. Also of economic interest is to facilitate harvesting, which is made possible by concentrating within a certain period of time the dehiscence, or reduction of adhesion to the tree, in citrus fruit, olives or other species and varieties of pome fruit, stone fruit and nuts. The same mechanism, i.e. the promotion of the development of abscission tissue between fruit part or leaf part and shoot part of the plants is also essential for the controlled defoliation of useful plants, in particular cotton. Moreover, a shortening of the time interval within which the individual cotton plants mature leads to an increased fiber quality after harvesting.

Moreover, it has been found that the formulations of the invention are also suitable for the control of conifers, in particular of conifer seedlings which grow naturally, and specifically for the control of pine seedlings which grow naturally.

In general, the liquid suspension concentrate formulations described herein are useful for combating undesired vegetation. For this purpose, the formulations may be applied as such or are preferably applied after dilution with water. Preferably, for various purposes of end user application, a so-called aqueous spray-liquor is prepared by diluting the suspension concentrate formulation of the present invention with water, e.g. tap water. The spray-liquors may also comprise further constituents in dissolved, emulsified or suspended form, for example fertilizers, active substances of other groups of herbicidal or growth-regulatory active substances, further active substances, for example active substances for controlling animal pests or phytopathogenic fungi or bacteria, furthermore mineral salts which are employed for alleviating nutritional and trace element deficiencies, and nonphytotoxic oils or oil concentrates. As a rule, these constituents are added to the spray mixture before, during or after dilution of the formulations according to the invention.

The formulations of the invention can be applied by the pre-emergence or the post-emergence method. If saflufenacil and/or glyphosate are less well tolerated by certain crop plants, application techniques may be employed where the herbicidal compositions are sprayed, with the aid of the spraying apparatus, in such a way that the leaves of the sensitive crop plants ideally do not come into contact with them, while the active substances reach the leaves of undesired plants which grow underneath, or the bare soil surface (post-directed, lay-by).

Depending on the aim of the control measures, the season, the target plants and the growth stage, the formulations of the invention are applied to such a degree that the application rates of saflufenacil are from 0.001 to 3.0, preferably from 0.01 to 1.0 kg/ha active substance (a.s.).

To widen the spectrum of action and to obtain synergistic effects, the liquid suspension concentrate formulations of the invention can be mixed with a large number of representatives of other groups of herbicidal or growth-regulatory active substances and applied together with these.

Examples of suitable mixing partners are 1,2,4-thiadiazoles, 1,3,4-thiadiazoles, amides, aminophosphoric acid and its derivatives, aminotriazoles, anilides, aryloxy/heteroaryloxyalkanoic acids and their derivatives, benzoic acid and its derivatives, benzothia-diazinones, 2-(hetaroyl/aroyl)-1,3-cyclohexanediones, heteroaryl aryl ketones, benzylisoxazolidinones, meta-$CF_3$-phenyl derivatives, carbamates, quinolinecarboxylic acid and its derivatives, chloroacetanilides, cyclohexenone oxime ether derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetero-aryloxyphenoxypropionic acid esters, phenylacetic acid and its derivatives, 2-phenyl-propionic acid and its derivatives, pyrazoles, phenylpyrazoles, pyridazines, pyridine-carboxylic acid and its derivatives, pyrimidyl ethers, sulfonamides, sulfonylureas, triazines, triazinones, triazolinones, triazolecarboxamides and uracils.

It is of also possible to use the liquid suspension concentrate formulations of the present invention as a tank-mix partner with other formulations. Thus, the formulations of the invention can be mixed and applied together with a large number of different pesticide compound formulations, for example those that include active ingredients or adjuvants, such as atrazine, glyphosate, glufosinate, S-metolachlor, 2,4-D ester, isoxaflutole, diflufenzopyr, dicamba, mesotrione, dimethenamid-P, pendimethalin, imazethapyr, paraffin oils, polyol fatty acid esters, polyethoxylated polyol fatty acid esters, ethoxylated alkyl aryl phosphates, methylated seed oils, emulsifiers, ammonium sulfate or mixtures thereof.

Moreover, it may be useful to apply the formulations of the invention, separately or in combination with other herbicides, jointly as a mixture with yet further plant protection agents, for example with agents for controlling pests or phytopathogenic fungi or bacteria.

The following examples are intended to further illustrate the present invention without limiting its scope in any way.

I. Analytics:

Particle sizes were determined by dynamic light scattering with a Malvern Mastersizer 2000 system at 23° C.

Viscosities were measured in analogy to DIN EN ISO 255 with a Brookfield DV-E Viscometer, spindle 1 of the RV spindle set at 50 m$^{-1}$. In addition, dynamic viscosities were determined in analogy to OECD Test Guidline 114 ("Viscosity of Liquids").

II. Ingredients:

Surfactant N1: polyethoxylated $C_{10}$-alcohol (11 EO units)— Lutensol® ON 110 (BASF SE);
Surfactant N2: polyethoxylated $C_{13}$-alcohol (3 EO units)— Lutensol® TO3 (BASF SE);
Surfactant N3: polyethoxylated castor oil (31 EO units)— Wettol® EM 31 (BASF SE);
Surfactant N4: polyethoxylated castor oil (40 EO units)— Emulsogen® EL 400 (Clariant);
Surfactant N5: polyethoxylated castor oil (40 EO units)— Emulan® EL 40 (BASF SE);

III. Preparation of the Compositions of the Invention:

General Procedure:

For each Example listed in table 3 either Diluent 3 or 4, as indicated in table 3, was introduced into a receiving vessel and saflufenacil anhydrate and glyphosate in the form indicated were added. After mixing with an Ultra-Turax®, the suspension was milled with the aid of a Dynomill® mill at a speed of approximately 3000 min$^{-1}$ and an exit temperature of 25 to 30° C. Thereafter, the mixture of surfactants N and A, as given in table 3, and either Diluent 1 or 2, if appropriate, were incorporated using an Ultra-Turrax®. Finally Dispersant 1, if appropriate, was added with stirring. After an optional additional milling step the oil suspension concentrate was stirred for further 20 minutes.

TABLE 3

| Components | Example: 1 | 2 | 3 | 4 | 5 | 6 | 7 | 8 | 9 |
|---|---|---|---|---|---|---|---|---|---|
| Saflufenacil anhydrate [g] | 58.9 | 58.9 | 58.9 | 58.9 | 56.8 | 58.1 | 58.9 | 29.4 | 29.4 |
| Glyphosate, acid form [g] | 373.3 | 373.3 | 373.3 | 373.3 | 359.8 | 367.8 | 395.3 | — | — |
| Glyphosate, ammonium salt [g]* | — | — | — | — | — | — | — | 387.0 | 387.0 |
| Surfactant N1 [g] | — | — | — | — | — | 99.0 | 100.3 | — | — |
| Surfactant N2 [g] | — | — | — | — | — | — | — | 20.0 | 20.0 |
| Surfactant N3 [g] | — | — | — | — | — | — | — | 120.0 | — |
| Surfactant N4 [g] | — | — | — | — | — | — | — | — | 120.0 |
| Surfactant N5 [g] | 100.0 | 200.0 | 100.0 | 100.0 | 63.9 | — | — | — | — |
| Surfactant A1 [g] | — | — | — | 200.0 | 137.5 | 75.8 | 76.6 | — | — |
| Surfactant A2 [g] | — | — | — | — | — | — | — | 60.0 | 60.0 |
| Surfactant A3 [g] | — | — | — | — | 50.0 | 50.0 | 50.0 | — | — |
| Surfactant A4 [g] | 100.0 | 100.0 | 100.0 | — | — | — | — | — | — |
| Dispersant 1 [g] | — | — | — | — | 25.5 | — | — | — | — |
| Diluent 1 [g] | — | — | — | 468.1 | — | — | — | 200.0 | 200.0 |
| Diluent 2 [g] | — | — | — | — | 207.5 | 207.5 | 188.9 | — | — |
| Diluent 3 [g] | 567.8 | 467.8 | — | — | 299.0 | 342.0 | 327.8 | — | — |
| Diluent 4 [g] | — | — | 567.8 | 504 | — | — | — | 296.0 | 296.0 |

*calculated as glyphosate acid form

Surfactant A1: Sodium salt of dioctyl sulfosuccinate in petroleum naphtha (70% (v/v))—Aerosol® OT-A (Cytec);
Surfactant A2 Calcium salt of dodecylbenzene sulfonate in 2-ethylhexan-1-ol (60% (v/v))—Wettol® EM 1 (BASF SE);
Surfactant A3 4-(sec-$C_{10}$-$C_{13}$-alkyl)-benzene sulfonic acid—Lutensit® A-LBS (BASF SE);
Surfactant A4 ammonium salt of polyethoxylated tristyryl phenyl ether sulfate (16 E0 units)—Soprophor® 4D 384 (Rhodia);
Diluent 1 methyl esters of saturated $C_{14}$-$C_{18}$-fatty acids and of mono-unsaturated $C_{16}$-$C_{18}$-fatty acids;
Diluent 2 dimethyl ester of adipinic acid;
Diluent 3 predominantly $C_{10}$- and $C_{11}$-alkyl benzenes within a boiling range of form 175 to 209° C., naphthaline depleted—Solvesso®150 ND (ExxonMobil Chemical);
Diluent 4 predominantly $C_{10}$- and $C_{14}$-alkyl naphthalines within a boiling range of form 235 to 305° C., naphthaline depleted—Solvesso®200 ND (ExxonMobil Chemical);
Dispersant 1: sodium carbonate;
Adjuvant 1: mixture of hydrocarbons and surfactants— Atplus 411 (ICI).

IV. Storage stability

The stabilities of stored formulations were evaluated on the basis of the quality of the emulsions/dispersions obtained therefrom by dilution.

Initially a sample of the formulation that was freshly prepared according to Example 9 was diluted with water (2 g in 98 g water) in analogy to the preparation of a spray liquor. A stable white emulsion/dispersion without sediment was obtained.

Samples of the formulation were then stored at 20° C., 30° C., 40° C. and 50° C., respectively, for a period of 6 months and afterwards diluted with water as described above. The resulting emulsions/dispersions were examined for their physical properties after storage for 2 hours at 20° C. In all cases no or only minor creaming/sedimentation accounting for less than 2% of the total weight of the saflufenacil was observed.

The chemical stability was assessed by determining the remaining proportion of intact saflufenacil anhydrite in the samples using HPLC. The results revealed that the active did not noticeably decompose.

In conclusion, the overall stability of the formulation of Example 9 at low to medium temperatures is good.

V. Herbicidal Activity of the Formulations According to the Invention

The effect of the oil suspension concentrate formulations according to the invention on the growth of undesirable plants was demonstrated by the following post-emergence treatment greenhouse experiments. For comparison purposes analogous experiments were carried out with a conventional formulation also containing saflufenacil and glyphosate.

1. Comparison to a Conventional Saflufenacil/Glyphosate Formulation

The test plants listed below were first grown, depending on the plant habit, to a height of 3 to 20 cm. Only then they were treated in parallel with spray liquors prepared from the formulation according to Example 9 or from a mixture of a glyphosate concentrate (Roundup SL, 360 g/L (Monsanto)) and wettable granules containing saflufenacil (Heat 70 WG (BASF) or Treevix WG (BASF), each containing 70% by weight of saflufenacil), respectively. In both cases the spray liquors were prepared by dilution with water to a level customary for saflufenacil and glyphosate. The test plant were sprayed using finely distributing nozzles to the extent that the application rates of saflufenacil and glyphosate given in table 4 were reached.

The test period extended over 34 days. During this time, the plants were tended, and their response to the treatments with active compound was evaluated.

The evaluation for the damage caused by the chemical compositions was carried out using a scale from 0 to 100%, compared to the untreated control plants. Here, 0 means no damage and 100 means complete destruction of the plants.

The plants used in the greenhouse experiments belonged to the following species:

| Scientific Name | Code | Common Name |
| --- | --- | --- |
| Gossypium hirsutum | GOSHI | cotton |
| Capsella bursa-pastoris | CAPBP | shepherd's-purse |
| Polygonum aviculare | POLAV | common knotgrass |
| Polygonum convolvus | POLCO | wild buckwheat |
| Lamium amplexicaule | LAMPU | henbit deadnettle |
| Stellaria media | STEME | common chickweed |
| Bidens pilosa | BIDPI | broom stick |
| Chenopodium album | CHEAL | fat hen |
| Cirsium arvense | CIRAR | creeping thistle |

Table 4 relates to the combined herbicidal activity of saflufenacil and glyphosate assessed 7, 21 and 34 days after treatment (DAT).

TABLE 4

Application in post-emergence of spray liquors prepared from the formulation of Example 9 and a conventional formulation

| | | application rate of glyphosate + saflufenacil | observed herbicidal activity [%] | |
| --- | --- | --- | --- | --- |
| Weed | DAT | [g/ha] | formulation of example 9 | conventional formulation |
| GOSHI | 7 | 75 + 6.25 | 90 | 70 |
| CAPBP | 7 | 150 + 12.5 | 80 | 65 |
| CAPBP | 21 | 150 + 12.5 | 90 | 45 |
| CAPBP | 34 | 150 + 12.5 | 98 | 40 |
| POLAV | 21 | 600 + 50 | 98 | 80 |
| POLAV | 34 | 600 + 50 | 100 | 60 |
| POLCO | 7 | 150 + 12.5 | 98 | 80 |
| POLCO | 34 | 150 + 12.5 | 100 | 55 |
| LAMPU | 7 | 600 + 50 | 90 | 75 |
| LAMPU | 34 | 600 + 50 | 100 | 75 |
| STEME | 7 | 75 + 6.25 | 80 | 65 |
| STEME | 34 | 75 + 6.25 | 65 | 40 |
| BIDPI | 7 | 75 + 6.25 | 95 | 90 |
| BIDPI | 27 | 75 + 6.25 | 70 | 55 |
| CHEAL | 34 | 150 + 12.5 | 80 | 70 |
| CIRAR | 6 | 150 + 12.5 | 85 | 80 |
| CIRAR | 27 | 150 + 12.5 | 100 | 70 |

2. Comparison to a Conventional Saflufenacil/Glyphosate Formulation in the Presence of an Additional Adjuvant The test plants listed below were first grown, depending on the plant habit, to a height of 3 to 20 cm. Only then they were treated in parallel with spray liquors prepared from the formulation according to Example 9 or from a mixture of a glyphosate concentrate (Roundup SL, 360 g/L (Monsanto)) and wettable granules containing saflufenacil (Heat 70 WG (BASF) or Treevix WG (BASF), each containing 70% by weight of saflufenacil), respectively. In both cases the spray liquors were prepared by first diluting with water to a level customary for saflufenacil and glyphosate and afterwards adding the adjuvant Atplus 411 (ICI, mixture of hydrocarbons and surfactants) in such amounts that application rates of 2 L/ha would be obtained. The test plant were sprayed with these spray liquors using finely distributing nozzles to the extent that the application rates of saflufenacil and glyphosate given in table 5 were reached.

The test period extended over 40 days. During this time, the plants were tended, and their response to the treatments with active compound was evaluated.

The evaluation for the damage caused by the chemical compositions was carried out using a scale from 0 to 100%, compared to the untreated control plants. Here, 0 means no damage and 100 means complete destruction of the plants.

The plants used in the greenhouse experiments belonged to the following species:

| Scientific Name | Code | Common Name |
| --- | --- | --- |
| Amaranthus retroflexus | AMARE | common tumble weed |
| Chenopodium album | CHEAL | fat hen |
| Echinochloa crus-galli | ECHCG | cockspur |

Table 5 relates to the combined herbicidal activity of saflufenacil and glyphosate assessed 7, 21 and 40 days after treatment (DAT).

TABLE 5

Application in post-emergence of spray liquors that include Adjuvant 1 and were prepared from the formulation of Example 9 and a conventional formulation

| | | application rate of glyphosate + saflufenacil | observed herbicidal activity [%] | |
| --- | --- | --- | --- | --- |
| Weed | DAT | [g/ha] | formulation of example 9 + Adjuvant 1 | conventional formulation + Adjuvant 1 |
| AMARE | 21 | 303 + 25 | 72 | 65 |
| AMARE | 7 | 605 + 50 | 85 | 78 |
| AMARE | 21 | 605 + 50 | 85 | 77 |
| AMARE | 40 | 605 + 50 | 60 | 43 |

TABLE 5-continued

Application in post-emergence of spray liquors that
include Adjuvant 1 and were prepared from the formulation
of Example 9 and a conventional formulation

| | | application rate | observed herbicidal activity [%] | |
|---|---|---|---|---|
| Weed | DAT | of glyphosate + saflufenacil [g/ha] | formulation of example 9 + Adjuvant 1 | conventional formulation + Adjuvant 1 |
| CHEAL | 7 | 605 + 50 | 87 | 80 |
| CHEAL | 21 | 605 + 50 | 94 | 83 |
| CHEAL | 40 | 605 + 50 | 62 | 50 |
| ECHCG | 7 | 605 + 50 | 73 | 63 |
| ECHCG | 21 | 605 + 50 | 82 | 70 |
| ECHCG | 40 | 605 + 50 | 72 | 65 |

As can be seen from tables 4 and 5 the formulation according to the invention shows clearly superior herbicidal activity against a variety of weed targets in comparison to a conventional formulation having the same levels of saflufenacil and glyphosate.

The invention claimed is:

1. A liquid suspension concentrate formulation for plant protection, comprising the components:
   a) 1 to 8% 2-chloro-5-[3,6-dihydro-3-methyl-2,6-dioxo-4-(trifluoromethyl)-1-(2H)pyrimidinyl]-4-fluoro-N-[[methyl(1-methylethyl)amino]sulfonyl]benzamide in the form of the anhydrite;
   b) 28 to 37% N-(phosphonomethyl)glycine in the form of its free acid, in the form of the ammonium salt or a substituted ammonium salt, or a mixture thereof;
   c) 30 to 55% at least one diluent selected from the group consisting of:
      c1) hydrocarbon solvents having a boiling point of at least 100° C.; and
      c2) $C_1$-$C_8$-alkyl esters of $C_8$-$C_{26}$-fatty acids, mono-, or di-$C_1$-$C_4$-alkyl amides of $C_8$-$C_{26}$-fatty acids;
   d) 0 to 20% optionally at least one additional diluent that differs from the at least one diluent c) and is selected an organic solvent having at least one oxygen atom;
   e) 3 to 20% at least one non-ionic surfactant comprising a polyalkoxylate moiety; and
   f) 2 to 22% at least one anionic surfactant containing a sulfonate group or a sulfate group; wherein the % of the components are based on the total weight of the formulation.

2. The liquid suspension concentrate formulation of claim 1, wherein the component b) is glyphosate ammonium salt.

3. The liquid suspension concentrate formulation of claim 1, wherein the weight ratio of component a) to component b) is in the range of from 1:3 to 1:16.

4. The liquid suspension concentrate formulation of claim 1, wherein the at least one additional diluent d) is selected from the group consisting of $C_4$-$C_{15}$-dialkyl dicarboxylic acid esters, N-$C_8$-$C_{15}$-alkyl pyrrolidones, $C_2$-$C_6$-lactones and DMSO.

5. The liquid suspension concentrate formulation of claim 1, wherein the one or more non-ionic surfactants of component e) are selected from the group consisting of polyethoxylates of $C_8$-$C_{22}$-alkanols and polyethoxylates of vegetable oils or animal fats.

6. The liquid suspension concentrate formulation of claim 5, wherein the component e) comprises at least two different non-ionic surfactants.

7. The liquid suspension concentrate formulation of claim 5, wherein the component e) comprises at least one polyethoxylate of a $C_8$-$C_{22}$-alkanol and at least one polyethoxylate of a vegetable oil.

8. The liquid suspension concentrate formulation of claim 5, wherein the one or more anionic surfactants of component f) are selected from the group consisting of polyethoxylates of mono-, di- and tristyrylphenylether sulfates, $C_1$-$C_{16}$-alkylbenzene sulfonates, $C_1$-$C_{16}$-alkynaphthalene sulfonates and $C_4$-$C_{18}$-dialkyl sulfosuccinates.

9. The liquid suspension concentrate formulation of claim 8, wherein the component f) comprises at least two different anionic surfactants.

10. The liquid suspension concentrate formulation of claim 1, wherein the hydrocarbon solvents c1) have a boiling point in the range of from 170 to 310° C.

11. The liquid suspension concentrate formulation of claim 1, wherein the at least one diluent c2) are selected from $C_1$-$C_8$-alkyl esters of $C_8$-$C_{26}$-fatty acids and di-$C_1$-$C_4$-alkyl amides of $C_8$-$C_{26}$-fatty acids.

12. The liquid suspension concentrate formulation of claim 1, wherein the at least one diluent c) is selected from hydrocarbon solvents c1).

13. The liquid suspension concentrate formulation of claim 1, wherein the at least one diluent c) is selected from $C_1$-$C_8$-alkyl esters of $C_8$-$C_{26}$-fatty acids, mono-, and di-$C_1$-$C_4$-alkyl amides of $C_8$-$C_{26}$-fatty acids.

14. The liquid suspension concentrate formulation of claim 1, wherein the component c) comprises at least one diluent c1) and at least one diluent c2).

15. A method of controlling undesired vegetation, comprising applying the liquid suspension concentrate formulation of claim 1, undiluted or in the form of an aqueous dilution, to plants, their environment or on seeds.

16. The method of claim 15, wherein the component b) of the formulation is glyphosate ammonium salt.

17. The method of claim 15, wherein the weight ratio of component a) to compound b) of the formulation is in the range of from 1:3 to 1:16.

18. The method of claim 15, wherein the at least one additional diluent d) of the formulation is selected from the group consisting of $C_4$-$C_{15}$-dialkyl dicarboxylic acid esters, N-$C_5$-$C_{15}$-alkyl pyrrolidones, $C_2$-$C_6$-lactones and DMSO.

19. The method of claim 15, wherein the one or more non-ionic surfactants of component e) of the formulation are selected from the group consisting of polyethoxylates of $C_8$-$C_{22}$-alkanols and polyethoxylates of vegetable oils or animal fats.

* * * * *

UNITED STATES PATENT AND TRADEMARK OFFICE
CERTIFICATE OF CORRECTION

PATENT NO. : 9,545,104 B2  
APPLICATION NO. : 13/513231  
DATED : January 17, 2017  
INVENTOR(S) : Michael Krapp et al.

Page 1 of 1

It is certified that error appears in the above-identified patent and that said Letters Patent is hereby corrected as shown below:

In the Claims

Column 21, Line 56, delete "N-$C_8$-$C_{15}$-alkyl" and replace with "N-$C_5$-$C_{15}$-alkyl"

Signed and Sealed this  
Sixth Day of June, 2017

Michelle K. Lee  
*Director of the United States Patent and Trademark Office*